United States Patent

Beriger et al.

[11] 3,943,202
[45] Mar. 9, 1976

[54] O-METHYL/ETHYL-S-PROPYL/BUTYL-O-PHENYL THIOPHOSPHATES AND DITHIOPHOSPHATES HAVING AN ETHER GROUP OR THE PHENYL RING

[75] Inventors: Ernst Beriger, Allschwil, Switzerland; Manfred Böger, Haltingen, Germany; Jozef Drabek, Allschwil; Odd Kristiansen, Reinach, both of Switzerland

[73] Assignee: Ciba-Geigy Corporation, Ardsley, N.Y.

[22] Filed: Dec. 20, 1974

[21] Appl. No.: 534,594

Related U.S. Application Data

[62] Division of Ser. No. 408,874, Oct. 23, 1973, Pat. No. 3,898,305.

[30] Foreign Application Priority Data

Nov. 3, 1972 Switzerland........................ 16043/72
Sept. 21, 1973 Switzerland........................ 13638/73

[52] U.S. Cl................................ 260/950; 260/951
[51] Int. Cl.²........................................... C07F 9/12
[58] Field of Search........................... 260/950, 951

[56] References Cited
UNITED STATES PATENTS

| | | | |
|---|---|---|---|
| 3,725,514 | 4/1973 | Tsuchiya et al. | 260/951 X |
| 3,825,636 | 7/1974 | Kishino et al. | 260/951 X |
| 3,839,511 | 10/1974 | Kishino et al. | 260/951 X |

*Primary Examiner*—Richard L. Raymond
*Attorney, Agent, or Firm*—Frederick H. Rabin

[57] ABSTRACT

Thiophosphoric and dithiophosphoric acid esters of the formula

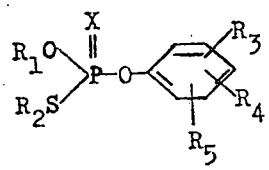

wherein $R_1$ represents methyl or ethyl, $R_2$ represents n-propyl, isobutyl or sec, butyl, $R_3$ and $R_4$ each represents chlorine, bromine, methyl or ethyl, $R_5$ represents —OCOCH₃, —O—C₃—C₅-alkenyl,
—O—C₃—C₅-alkinyl, —O—C₁—C₄-alkylene-
O—C₁—C₄-alkyl, —O—CH₂—CCl=CH₂, —O—CH₂—CH=CHCl, —SCH₂— 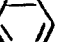 , —S—C₃—C₅-alkenyl, SCN, —CH₂—CCl=CH₂,
—CH₂CH=CHCl, —CHO, 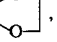 ,

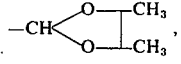

, 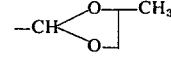 ,

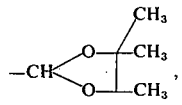

, 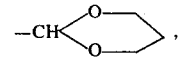 ,

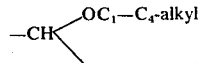

, 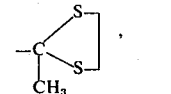 ,

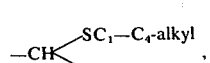

, 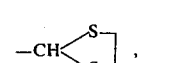 ,

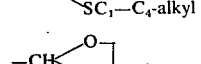

, 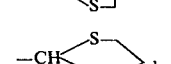 ,

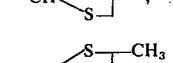

, 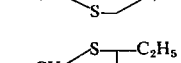 ,

—CH=N—, —CH=N—C₁—C₄-alkyl,

—CH=N—NH—C₁—C₄-alkyl or

—CH=N—N⟨C₁—C₄-alkyl / C₁—C₄-alkyl and

X represents oxygen or sulphur, processes for their manufacture and their use in pest control.

6 Claims, No Drawings

O-METHYL/ETHYL-S-PROPYL/BUTYL-O-PHENYL THIOPHOSPHATES AND DITHIOPHOSPHATES HAVING AN ETHER GROUP OR THE PHENYL RING

This is a division of application Ser. No. 408,874 filed on Oct. 23, 1973, now U.S. Pat. No. 3,898,345

The present invention relates to thiophosphoric and dithiophosphoric acid esters, process for their manufacture, and to their use in pest control.

The thiophosphoric and dithiophosphoric acid esters have the formula

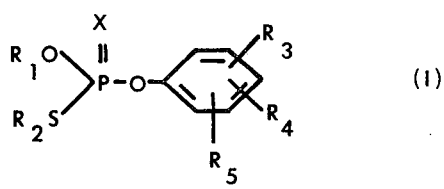

(I)

wherein $R_1$ represents methyl or ethyl, $R_2$ represents n-propyl, isobutyl or sec, butyl, $R_3$ and $R_4$ each represents chlorine, bromine, methyl or ethyl, $R_5$ represents

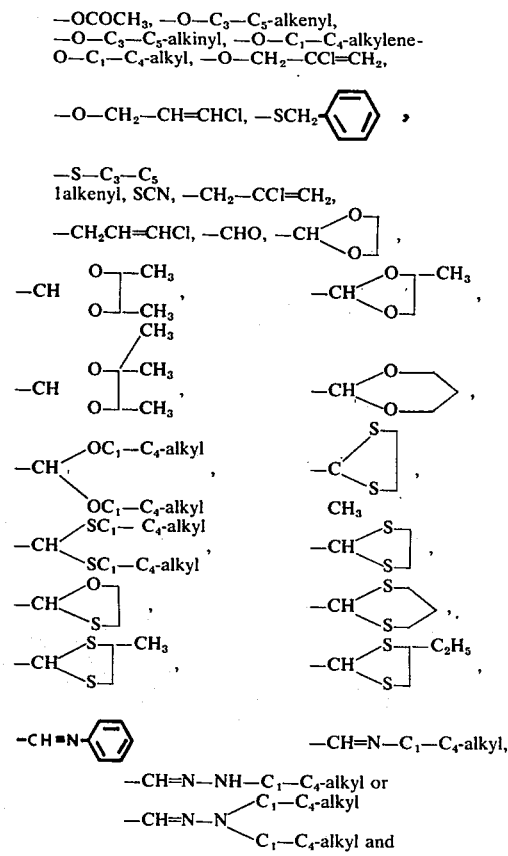

X represents oxygen or sulphur.

The alkenyloxy, alkinyloxy, alkoxyalkyleneoxy, or alkenylthio groups possible for $R_5$ can be straight-chain or branched. Examples of such groups include: allyloxy, methallyloxy, proparglyloxy, 1-methyl-2-propinyloxy, 1,1-dimethyl-2-propinyloxy, (1-methyl-2-methoxy)-ethoxy, 2-methoxy-ethoxy,2-methoxy-ethoxy, 2-ethoxy-ethoxy, allylthio, methallylthio.

The alkyl moieties of an acetal, thioacetal, n-alkylformimino, N-alkylhydrazono or N,N-dialkylhydrazono group $R_5$ are straight-chain. Examples of such alkyl moieties include: methyl, ethyl.

A preferred group of compounds is that of the formula I, wherein $R_1$ represents methyl or ethyl, $R_2$ represents n-propyl or sec. butyl, $R_3$ and $R_4$ each represents hydrogen, chlorine, bromine, methyl or ethyl, $R_5$ represents allyloxy, methallyloxy, 2-chloroallyloxy, 3-chloroallyloxy, propargyloxy, allylthio or methallylthio, and X represents oxygen.

A further preferred group of compounds of the formula I is that wherein $R_1$ represents methyl or ethyl, $R_2$ represents n-propyl or sec. butyl, $R_3$ and $R_4$ each represents hydrogen, chlorine, bromine, methyl or ethyl, $R_5$ represents

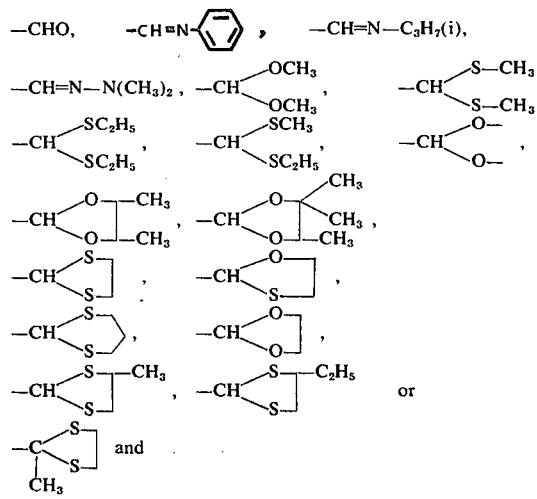

X represents oxygen.

Yet a further preferred group of compounds of the formula I is that wherein $R_1$ represents methyl or ethyl, $R_2$ represents n-propyl or sec. butyl, $R_3$ and $R_4$ each represents hydrogen, chlorine, bromine, methyl or ethyl, $R_5$ represents 2-chloroallyl or 3-chloroallyl, and X represents oxygen.

Particularly to be highlighted on account of their action are the compounds of the formula I wherein $R_1$ represents ethyl, $R_2$ represents n-propyl or sec. butyl, $R_3$ and $R_4$ each represents hydrogen, chlorine, bromine or methyl, and $R_5$ is in ortho-position and represents 2-chloroallyl or 3-chloroallyl, and X represents oxygen.

The compounds of the formula I can be manufactured by methods which are known per se, e.g. in the following manner:

1a)

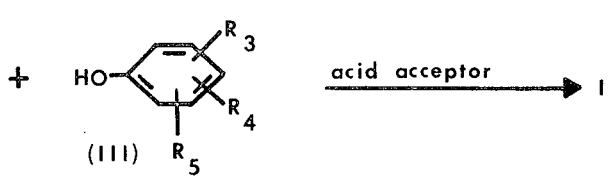

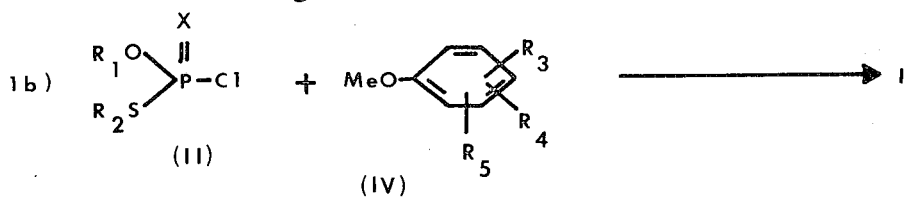

In the formulae II, III and IV, $R_1$ to $R_5$ and X have the meanings given for the formula I and Me represents an alkali metal, in particular sodium or potassium, ammonium or alkylammonium.

Process 1a and 1b can be carried out at normal pressure, at a temperature of 0°–80°C, preferably 20°–50°C, and in solvents and diluents that are inert towards the reactants.

Examples of suitable solvents or diluents are: ether and ethereal compounds, such as diethyl ether, dipropyl ether, dioxan, tetrahydrofuran; amides, such as N,N-dialkylated carboxy amides; aliphatic, aromatic, and halogenated hydrocarbons, in particular benzene, toluene, xylene, chloroform, chlorobenzene; nitriles, such as acetonitrile.

The starting materials of the formula II are known and can be manufactured by a method analogous to e.g. that described in J. Org. Chem. 30 3217 (1965).

The active substances of the formula I are suitable for combating animal and plant pests of the most diverse kinds. In particular, they act effectively against all development states, such as eggs, larvae, nymphs, pupae, and adults of insects, e.g. of the families:

Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleriidae, Culcidae, Tipulidae, Stomoxydae, Muscidae, Calliphoridae, Trypetidae, Pulicidae.

The compounds of the formula I are also active against eggs, larvae, and adults of representatives of the order Acarina, such as mites, spider mites, and ticks, e.g. of the families: Ixodidae, Argasidae, Tetranychidae, and Demanyssidae.

The insecticidal or acaricidal action can be substantially broadened and adapted to given circumstances by addition of other insecticides and/or acaricides. Examples of suitable additives are: organic phosphorus compounds, derivatives of nitrophenols, formamidines, ureas, carbamates, and chlorinated hydrocarbons.

In addition to the above cited properties, the compounds of the formula I are also active against fungi, for exampel against the phytopathogenic fungi of the classes: Oomycetes, Zygomycetes, Ascomycetes, Basidiomycetes, Denteromycetes. They are also active against phytopathogenic nematodes.

The compounds of the formula I may be used as pure active substance or together with suitable carriers and/or additives. Suitable carriers and additives can be solid or liquid and correspond to the substances conventionally used in formulation technology, for example natural or regenerated substances, solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology.

The agents according to the invention are manufactured in known manner by intimately mixing and/or grinding active substances of the formula I with the suitable carriers, optionally with the addition of dispersants or solvents which are inert towards the active substances. The active substances may take, and be used in, the following forms:

Solid forms:
Dusts, tracking agents, granules, coated granules, impregnated granules and homogeneous granules.

Liquid forms:
a. active substances which are dispersible in water: wettable powders, pasts, emulsions;
b. solutions.

The content of active substance in the above described agents is between 0.1% to 95%, in which connection it should be mentioned that, in the case of application from aircraft or some other suitable means of application, it is possible to use concentrations of up to 99.5%.

The active substances of the formula I can, for example, be formulated as follows:

Dusts

The following substances are used to manufacture (a) a 5% and (b) a 2% dust:
a. 5 parts of active substance
  95 parts of talcum
b. 2 parts of active substance
  1 part of highly disperse silicic acid
  97 parts of talcum.

The active substances are mixed with the carriers and ground.

Granules

The following substances are used to produce 5% granules:
  5 parts of active substance,
  0.25 parts of epichlorohydrin,
  0.25 parts of cetyl polyglycol ether,
  3.50 parts of polyethylene glycol,
  91 parts of kaolin (particle size 0.3 – 0.8 mm).

The active substance is mixed with epichlorohydrin and dissolved with 6 parts of acetone; the polyethylene glycol and cetyl polyglycol ether are then added. The thus obtained solution is sprayed on kaolin, and the acetone subsequently evaporated in vacuo.

Wettable powder

The following constituents are used for the preparation of (a) a 40%, (b) and (c) a 25%, and (d) a 10% wettable powder:
a. 40 parts of active substance,
  5 parts of sodium lignin sulphonate,
  1 part of sodium dibutyl-naphthalene sulphonate,
  54 parts of silicic acid.
b. 25 parts of active substance,
  4.5 parts of calcium lignin sulphonate,
  1.9 parts of Champagne chalk/hydroxyethyl cellulose mixture (1:1),
  1.5 parts of sodium dibutyl naphthalene sulphonate, 19.5 parts of silicic acid,
19.5 parts of Champagne chalk,
28.1 parts of kaolin
c. 25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselgur
46 parts of kaolin.
d. 10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to produce (a) a 10% and (b) a 25% emulsifiable concentrate:
a. 10 parts of active substance,
3.4 parts of epoxidised vegetable oil,
13.4 parts of a combination emulsifier consisting of fatty alcohol polyglycol ether and alkylaryl sulphonate calcium salt,
40 parts of dimethylformamide,
43.2 parts of xylene,
25 parts of active substance, 2.5 parts of epoxidised vegetable oil,
10 parts of an alkylarylsulphonate/fatty alcoholglycol ether mixture,
5 parts of dimethylformamide,
57.5 parts of xylene.

From these concentrates it is possible to produce, by dilution with water, emulsions of any desired concentration.

Spray

The following constituents are used to prepared a 5% spray:
5 parts of active substance,
1 part of epichlorohydrin,
94 parts of benzene (boiling limits 160°C-190°C).

EXAMPLE 1

Manufacture of O-ethyl-S-(n)-propyl-O-4-formylphenyl-thiophosphoric acid ester 13.3 g of triethylamine are added to a solution of 17 g of 4-hydroxybenzaldehyde in 150 ml of benzene. 26.4 g of O-ethyl-S-(n)-propyl-chlorothiolphosphoric acid ester are added dropwise with constant stirring at 10°-15°C. The reaction mixture is stirred for 12 hours at room temperature, then it is washed with water, 3% $Na_2CO_3$ solution, and again with water, and dried over anhydrous sodium sulphate. The benzene is distilled off. Molecular distillation of the residue yields the compound of the formula

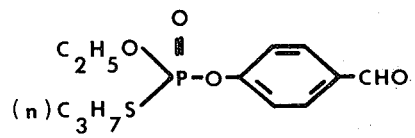

with a refractive index of $n_D^{23} = 1.5350$.

The following compounds are also manufactured in analogous manner:

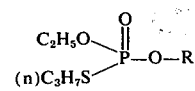

| R | Physical Data |
|---|---|
| ![]-CHO with OCH₃ | $n_D^{23} = 1,540$ |
| Cl, Cl, CHO substituted phenyl | $n_D^{23} = 1,5460$ |
| -⟨⟩-CH=N-N(CH₃)₂ | $n_D^{23} = 1,5435$ |
| CH=N-N(CH₃)₂, Cl substituted phenyl | $n_D^{23} = 1,5786$ |
| -⟨⟩-CH=N-⟨⟩ | $n_D^{20} = 1,5921$ |

-continued

| R | Physical Data |
|---|---|
|  3-CHO phenyl | $n_D^{20} = 1.5320$ |
| 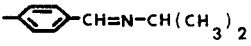 4-CH=N-CH(CH$_3$)$_2$ phenyl | $n_D^{20} = 1.5293$ |
|  4-Br, 3-CHO phenyl | $n_D^{20} = 1.5526$ |
| 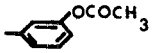 2-CHO phenyl | $n_D^{23} = 1.5290$ |
| 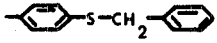 3-CHO, 5-Br phenyl | $n_D^{23} = 1.5584$ |
|  2-OCOCH$_3$ phenyl | $n_D^{23} = 1.5152$ |
|  2-OCOCH$_3$, 4-Cl phenyl | $n_D^{22} = 1.5242$ |
|  4-S-CH$_2$-phenyl phenyl | $n_D^{20} = 1.5762$ |
|  4-S-CH$_2$-phenyl, 3-CH$_3$ phenyl | $n_D^{20} = 1.5806$ |
|  phenyl-CH(S-)(S-) (dithiolane) | $n_D^{22} = 1.5791$ |
|  phenyl-CH(O-)(O-) (dioxolane) | $n_D^{20} = 1.5254$ |
| phenyl-CH(O-)(O-) with CH$_3$, CH$_3$ | $n_D^{20} = 1.5131$ |
| phenyl-CH(O-)(O-) with CH$_3$, CH$_3$, CH$_3$ | $n_D^{20} = 1.5129$ |

-continued

| R | Physical Data |
|---|---|
| phenyl-CH with 1,3-dioxolane, para-Br | $n_D^{20} = 1.566 - 1.568$ |
| phenyl-CH with 1,3-dioxane | $n_D^{20} = 1.5295$ |
| phenyl-CH(OCH$_3$)$_2$ | $n_D^{20} = 1.5110$ |
| para-CH$_3$-phenyl-CH(SCH$_3$)$_2$ | $n_D^{20} = 1.5625$ |
| phenyl-CH(SCH$_3$)$_2$, para-Cl | $n_D^{20} = 1.5674$ |
| phenyl-CH with 1,3-dithiolane | $n_D^{20} = 1.5783$ |
| phenyl-CH with 1,3-dithiolane, C$_2$H$_5$ substituent | $n_D^{20} = 1.5698$ |
| phenyl-CH with 1,3-dithiolane, CH$_3$ substituent | $n_D^{20} = 1.5765$ |
| phenyl-CH with 1,3-dithiane | $n_D^{20} = 1.587$ |

-continued
| R | Physical Data |
|---|---|
| 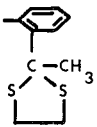 | $n_D^{20} = 1,5705$ |
| 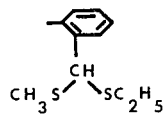 | $n_D^{20} = 1,5600$ |
| 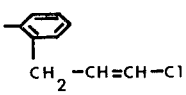 | $n_D^{20} = 1,5346$ |
| 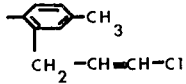 | $n_D^{20} = 1,5318$ |
| 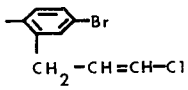 | $n_D^{20} = 1,5532$ |
| 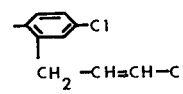 | $n_D^{20} = 1,5400$ |
| 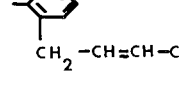 | $n_D^{20} = 1,5419$ |
| 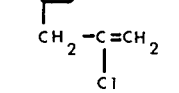 | $n_D^{20} = 1,5299$ |
| 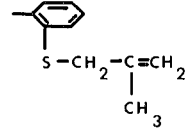 | $n_D^{20} = 1,5489$ |
| 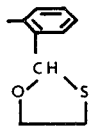 | $n_D^{20} = 1,5542$ |
| 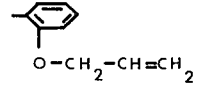 | $n_D^{20} = 1,5245$ |

-continued
| R | Physical Data |
|---|---|
|  | $n_D^{20} = 1,5220$ |
|  | $n_D^{20} = 1,5225$ |
|  | $n_D^{20} = 1,5308$ |
|  | $n_D^{20} = 1,5290$ |
|  | $n_D^{20} = 1,5298$ |
|  | $n_D^{20} = 1,5219$ |
|  | $n_D^{20} = 1,5334$ |
|  | $n_D^{20} = 1,5244$ |
|  | $n_D^{20} = 1,5102$ |
|  | $n_D^{20} = 1,5430$ |
|  | $n_D^{20} = 1,5372$ |
|  | $n_D^{20} = 1,5530$ |
|  | $n_D^{20} = 1,5591$ |

15 -continued
| R | Physical Data |
|---|---|
| 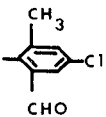 | $n_D^{20} = 1,5418$ |
| 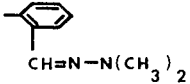 | $n_D^{20} = 1,5669$ |
| 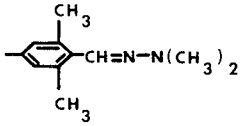 | $n_D^{20} = 1,5565$ |
| 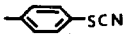 | $n_D^{22} = 1,5489$ |
|  | $n_D^{22} = 1,5568$ |
| 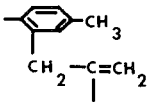 | $n_D^{20} = 1,5272$ |
| 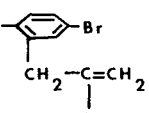 | $n_D^{20} = 1,5681$ |
| 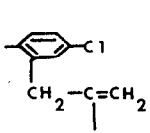 | $n_D^{20} = 1,5355$ |
In addition, the following compounds are manufactured in analogous manner:
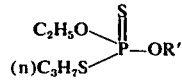
| R' | Physical Data |
|---|---|
| 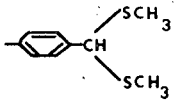 | $n_D^{20} = 1,5862$ |
| 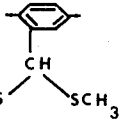 | $n_D^{20} = 1,5890$ |
| 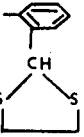 | $n_D^{20} = 1,598 - 1,599$ |

-continued
| R¹ | Physical Data |
|---|---|
| 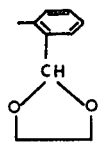 | $n_D^{20} = 1,5527$ |
| 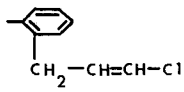 | $n_D^{20} = 1,5549$ |
| 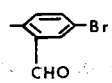 | $n_D^{23} = 1,5824$ |
| 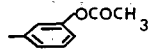 | $n_D^{22} = 1,5454$ |
The following compounds are also manufactured in analogous manner:
| Compound | Physical Data |
|---|---|
| (i)C₄H₉S–P(=O)(OC₂H₅)–O–C₆H₄–SCN | $n_D^{22} = 1,5412$ |
| (sec.)C₄H₉S–P(=O)(OC₂H₅)–O–C₆H₄–SCN | $n_D^{22} = 1,5402$ |
| (i)C₄H₉S–P(=O)(OC₂H₅)–O–C₆H₄–CH₂–CH=CH–Cl | $n_D^{20} = 1,5284$ |
| (sec.)C₄H₉S–P(=O)(OC₂H₅)–O–C₆H₄–CH₂–CH=CH–Cl | $n_D^{20} = 1,5313$ |
| (i)C₄H₉S–P(=O)(OC₂H₅)–O–C₆H₄–CH₂–C(Cl)=CH₂ | $n_D^{20} = 1,5240$ |

-continued

| Compound | Physical Data |
|---|---|
| 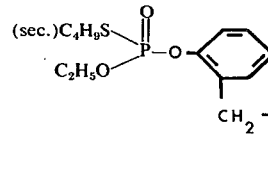 | $n_D^{20} = 1.5273$ |
| 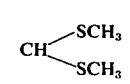 | $n_D^{20} = 1.5625$ |
| (sec.)C₄H₉S–P(=O)(OC₂H₅)–O–C₆H₄–CH(SCH₃)₂ | $n_D^{20} = 1.5605$ |

EXAMPLE 2

A. Insecticidal ingest poison action

Tobacco plants were sprayed with a 0.05% aqueous emulsion (obtained from a 10% emulsifiable concentrate). After the coating had dried, the tobacco plants were populated with Spodoptera littoralis larvae $L_3$ and with Heliothis virescens larvae $L_3$. The test was carried out at 24°C and 60% relative humidity. In the above test, the compounds according to Example 1 exhibited good ingest poison action against Spodoptera littoralis and Heliothis virescens.

B. Insecticidal contact action

Broad beans (vicia faba) reared in pots were infected with about 200 leaflice (Aphis fabae) per plant one day before the application. A spray broth in a concentration of 1000 ppm (prepared from a 25% wettable powder) was applied to the leaves populated with lice using a compressed air spray. Evaluation took place 24 hours after the application. In the above test, the compounds according to Example 1 exhibited good contact action against Aphis fabae.

EXAMPLE 3

Action against Chilo suppressalis

Six rice plants at a time of the variety Caloro' were transplanted into plastic pots (diameter at the top = 17 cm) and reared to a height of about 60 cm. Infestation with Chilo suppressalis larvae ($L_1$: 3–4 mm long) took place 2 days after the active substance had been applied in granule form to the paddy water (rats of application: 8 kg of active substance per hectare). Evaluation of the insecticidal action took place 10 days after application of the granules.

The compounds according to Example 1 were active in the above test against Chilo suppressalis.

EXAMPLE 4

Action against ticks
A. Rhipicephalus bursa

Five adult ticks and 50 tick larvae were counted into a glass tube and immersed for 1 to 2 minutes in 2 ml of an aqueous emulsion from an emulsion series each containing 100, 10, 1 and 0.1 ppm of test substance. The tube was then sealed with a standardised cotton wool plug and placed on its head, so that the active substance emulsion could be absorbed by the cotton wool.

In the case of the adults evaluation took place after 2 weeks, and in that of the larvae after 2 days. Each test was repeated twice.

B. Boophilus microplus (larvae)

Tests were carried out in each case with 20 OP-sensitive larvae using a dilution series analogous to that of test A. (The resistence refers to the tolerability of Diazinon).

The compounds according to Example 1 acted well in these tests against adults and larvae of Thipicephalus bursa and larvae of Boophilus microplus.

EXAMPLE 5

Action against spider mites

Phaseolus vulgaris (dwarf beans) had an infested piece of leaf from a mass culture of Tetranychus urticae placed on them 12 hours before the test for the acaricidal action. The mobile stages which had migrated were sprayed with the emulsified test preparations from a chromatography atomiser so that the spray broth did not run off. The number of living and dead larvae, adults and eggs were evaluated after 2 to 7 days under a stereoscopic microscope and the result was expressed in percentages. During the "interim," the treated plants were kept in greenhouse compartments at 25°C.

The compounds according to Example 1 were active in the above test against eggs, larvae and adults of Tretranychus urticae.

We claim:

1. A compound of the formula

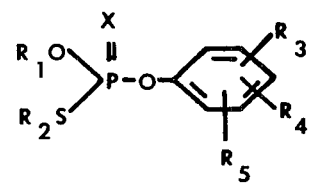

wherein $R_1$ represents methyl or ethyl, $R_2$ represents n-propyl, isobutyl or sec. butyl, $R_3$ and $R_4$ each represents hydrogen, chlorine, bromine, methyl or ethyl, $R_5$ represents —O-C$_3$-C$_5$—alkenyl, —O-C$_3$-C$_5$—alkinyl, —O-C$_1$-C$_4$—alkylene—O-C$_1$-C$_4$—alkyl, —O-CH$_2$—CCl=CH$_2$, —O-CH$_2$-CH=CHCl,

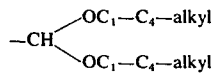

and X represents oxygen or sulphur.

2. A compound according to claim 1, wherein R$_2$ represents n-propyl or sec. butyl, R$_5$ represents allyloxy, methallyloxy, 2-chloroallyloxy, 3-chloroallyloxy or propargyloxy, and X represents oxygen.

3. A compound according to claim 1, wherein R$_2$ represents n-propyl or sec. butyl, R$_5$ represents

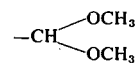

and X represents oxygen.

4. O-ethyl-S-n-propyl-O-[(2-(3-chloroallyloxy)-phenyl]-thiolphosphate, according to claim 2.

5. O-ethyl-S-n-propyl-O-[2-(2-chloroallyloxy)-phenyl]-thiolphosphate, according to claim 2.

6. O-ethyl-S-n-propyl-O-[2-(2-methoxy-1-methylethoxy)thiolphosphate according to claim 1.

* * * * *

UNITED STATES PATENT OFFICE
CERTIFICATE OF CORRECTION

Patent No. 3,943,202  Dated March 9, 1976

Inventor(s) Ernst Beriger et al.

It is certified that error appears in the above-identified patent and that said Letters Patent are hereby corrected as shown below:

Claim 6 in column 22 should read as follows:

O-ethyl-S-n-propyl-O-[2-(2-methoxy-1-methylethoxy)-phenyl]-thiolphosphate according to Claim 1.

Signed and Sealed this

*fifteenth* Day of *June 1976*

[SEAL]

Attest:

RUTH C. MASON
*Attesting Officer*

C. MARSHALL DANN
*Commissioner of Patents and Trademarks*